United States Patent [19]

Olerud

[11] Patent Number: 4,827,918
[45] Date of Patent: May 9, 1989

[54] FIXING INSTRUMENT FOR USE IN SPINAL SURGERY

[76] Inventor: Sven Olerud, S-740 11, Lännaholm, Sweden

[21] Appl. No.: 51,960
[22] PCT Filed: Aug. 14, 1986
[86] PCT No.: PCT/SE86/00365
§ 371 Date: May 6, 1987
§ 102(e) Date: May 6, 1987
[87] PCT Pub. No.: WO87/01026
PCT Pub. Date: Feb. 26, 1987

Related U.S. Application Data

[63] Continuation-in-part of Ser. No. 808,119, Dec. 12, 1985, abandoned.

[30] Foreign Application Priority Data

Aug. 15, 1985 [SE] Sweden .............................. 8503828

[51] Int. Cl.$^4$ .............................................. A61B 17/18
[52] U.S. Cl. .......................... 128/92 YM; 128/92 ZW; 402/116
[58] Field of Search .................. 403/116, 117; 128/69, 128/92 YM, 92 ZW, 92 ZZ, 92 Z, 92 ZY; 254/100

[56] References Cited

U.S. PATENT DOCUMENTS

| | | | |
|---|---|---|---|
| 2,251,209 | 7/1941 | Stader | 128/92 Z |
| 2,333,033 | 10/1943 | Mraz | 128/92 ZZ |
| 2,391,693 | 12/1945 | Ettinger | 128/92 Z |
| 2,393,795 | 1/1946 | Miller . | |
| 2,432,695 | 12/1947 | Speas | 128/92 ZW |
| 3,401,951 | 9/1968 | Bloom | 403/116 |
| 4,271,832 | 6/1981 | Evan et al. | 128/92 ZW |
| 4,274,401 | 6/1981 | Miskew | 128/92 YM |
| 4,386,603 | 6/1983 | Mayfield | 128/69 |
| 4,611,582 | 9/1986 | Duff | 128/69 |
| 4,658,809 | 4/1987 | Ulrich et al. | 128/92 YM |

FOREIGN PATENT DOCUMENTS

| | | | |
|---|---|---|---|
| 3219575 | 12/1983 | Fed. Rep. of Germany | 128/92 YM |
| 1022702 | 6/1983 | U.S.S.R. | |
| 8302554 | 8/1983 | World Int. Prop. O. | 128/92 ZW |

OTHER PUBLICATIONS

Bulletin No. 70; Experimental: Fixateur, Interne für de Wirbelsäule.

*Primary Examiner*—Dalton L. Truluck
*Assistant Examiner*—Denise Whelton
*Attorney, Agent, or Firm*—Finnegan, Henderson, Farabow, Garrett & Dunner

[57] ABSTRACT

A fixing instrument intended to adjust and lock in adjusted position vertebrae in relation to each other includes a unit comprising two support members which are mutually connected by means of a screw spindle extending through said support members such that the support members are moved towards each other upon rotation of the screw spindle in one direction and away from each other upon rotation in the opposite direction. The support members are pivotally connected to securing members which by means of bone screws are intended to be secured each to a vertebra. The pivot stud has a transverse hole through which extends a locking screw threaded into the support member and having a tapered part by means of which it in active screwed in position by abutment against the wall portion which surrounds the hole in the stud presses the securing member and the support member against each other. Since the bone screw extends through an opening in the support member which is open in the direction facing the support member such that the periphery of the bone screw will be located outside the surface of the securing member a locking of the bone screw is also accomplished when the locking screw is tightened. The bone screw further has a plurality of circumferential grooves and the securing member has a turning bolt provided with a projection which can penetrate into one of said grooves for fixing the bone screw against displacement. All of these lockings thus are carried out from one single position. Instead of the transverse hole (11) the stud may have an annular groove with a tapered limiting surface with which two locking screws may cooperate.

12 Claims, 3 Drawing Sheets

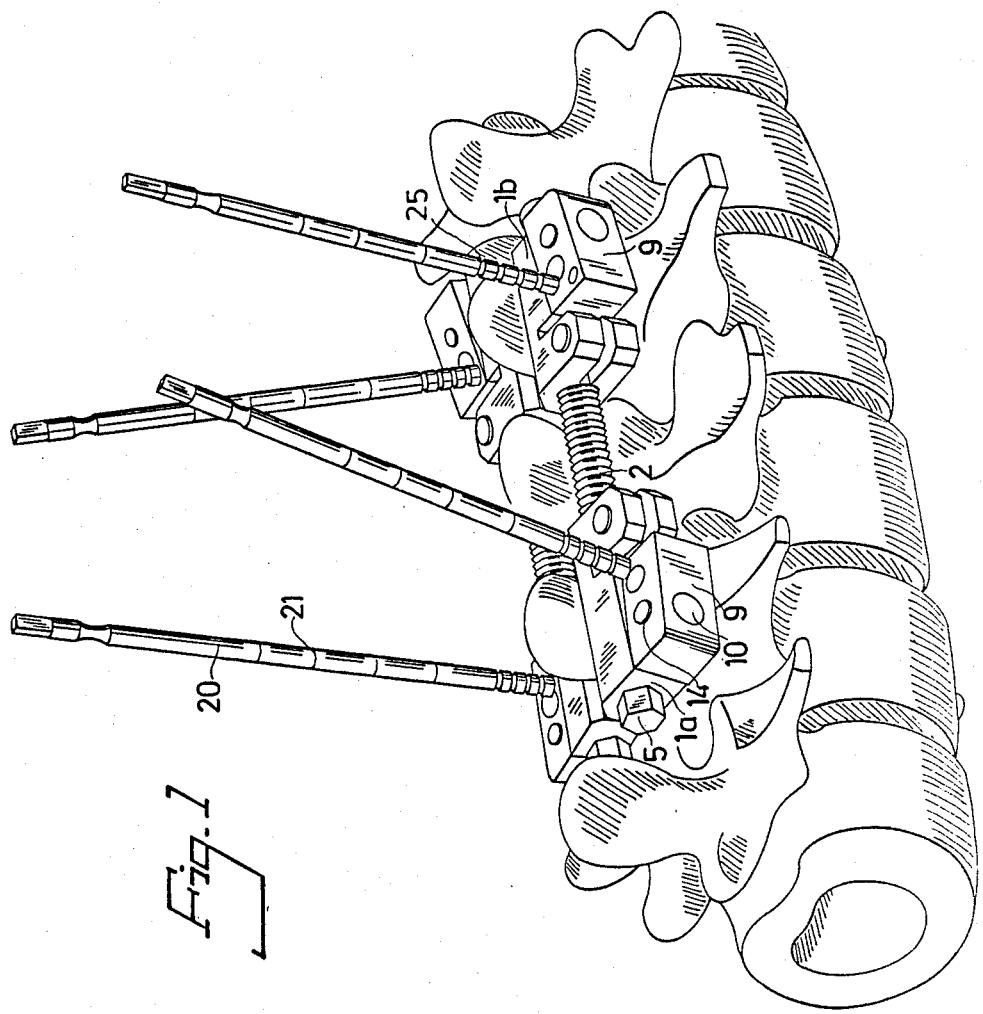

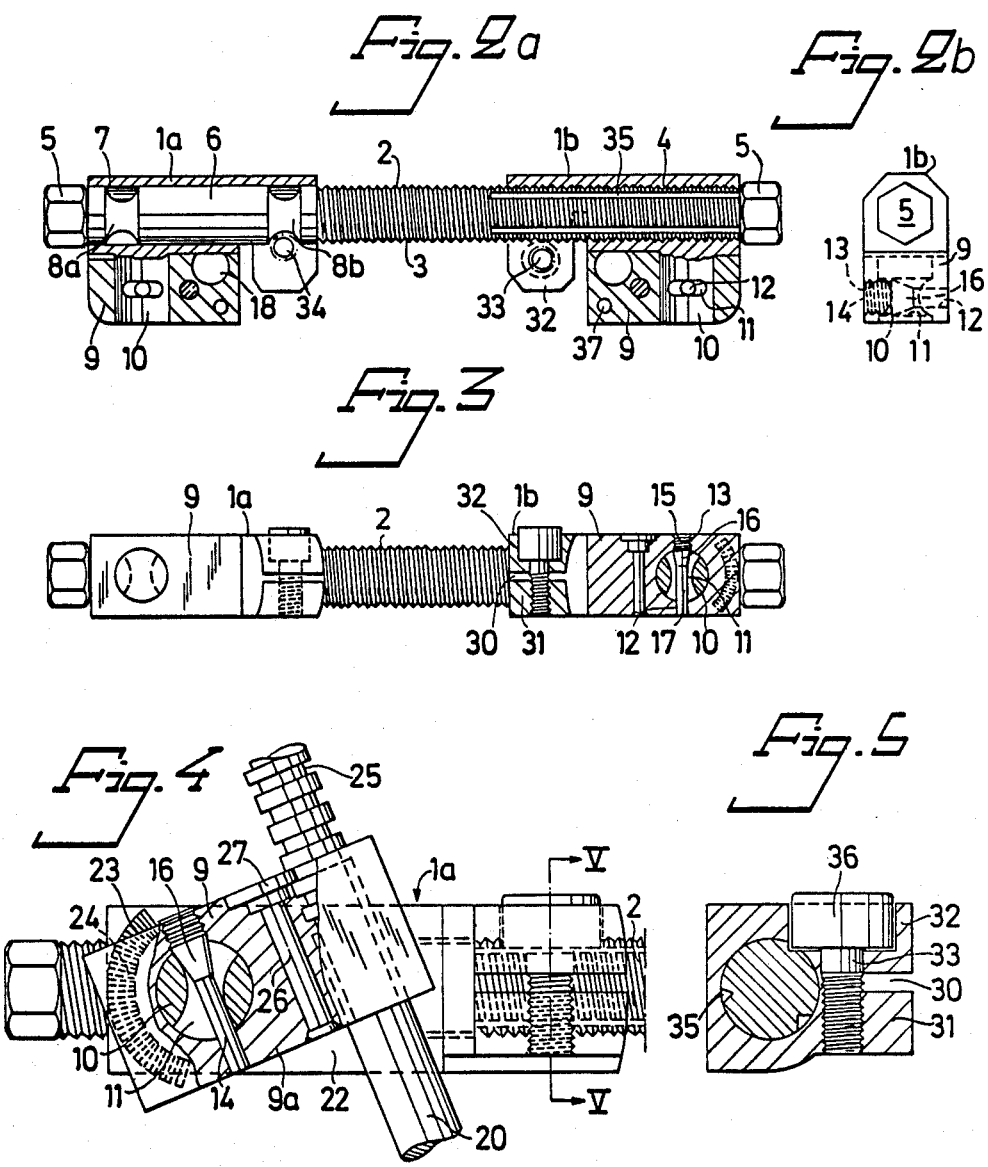

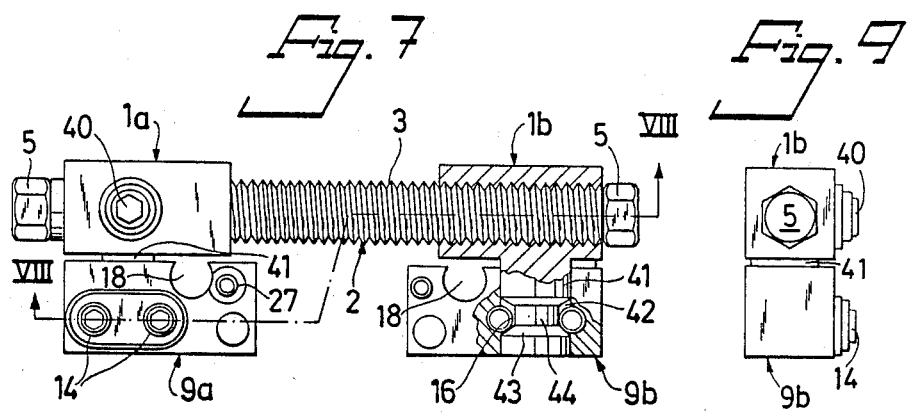
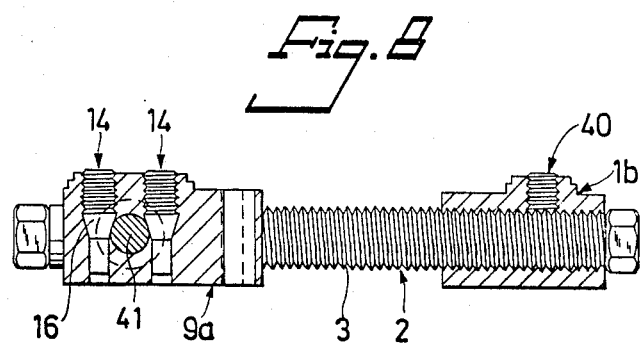

FIXING INSTRUMENT FOR USE IN SPINAL SURGERY

This application is a continuation-in-part of application Ser. No. 808,119, filed Dec. 12, 1985 now abandoned.

The present invention refers to a fixing instrument which is intended to secure two vertebrae in position relative to each other also in cases when one or several vertebrae remain unfixed between said vertebrae.

More specifically the invention refers to fixing instruments which include two support members which are so connected to each other by means of a screw spindle that they will move towards each other when the screw spindle is rotated in one direction and away from each other when the screw spindle is rotated in the opposite direction and where each of said support members is pivoted to a securing member which is provided to be secured to a vertebrae at least by means of a screw provided to pass through an opening in said securing member.

In instruments of the kind referred to it is of utmost importance that every adjustment can be secured rapidly and effectively and for such a purpose special locking or fixing constructions are used.

A serious drawback of the instruments referred to and now on the market is that said constructions are so designed that the surgeon has to work from various directions and also deep in the body of the patient. In order to lock the securing members in place relative to the members bolts with nuts are used which makes it necessary to operate one wrench at the front side of the instrument and one at the back side thereof. The screw spindle is further threaded in both ends which means that also in this respect the surgeon has to operate two wrenches, one at each end of the instrument. It is self-explanatory that such an operation is time consuming and troublesome and that the encroachment in the back of the patient has to be unnecessarily extensive. The constructions known in the art further—in spite of a complicated structure—lack sufficient security and effectiveness, partly upon the fact that they have an unsatisfactory stability as refers to turning.

Thus, the primary object of the invention has been to provide a simple and sturdy instrument of the kind referred to, by means of which a safe and effective fixing is obtained and which is designed so as to make it possible for the surgeon to accomplish the necessary lockings from one single position and in a very simple manner, i.e. by tightening screws or similar fastening elements, at the same time offering the advantage of a reduced encroachment in the back of the patient.

To accomplish this and other objectives the invention has the characteristics specified in the claims.

The accompanying drawings illustrate by way of example an embodiment of the invention and a modified locking system between the support members and the securing members and more particularly:

FIG. 1 shows in perspective from the rear and side some spinal vertebrae with two instruments according to the invention arrangement for adjusting displacement of two vertebrae.

FIGS. 2(a) and 2(b) respectively illustrate one of said instruments in a plan view and end view, partly in section.

FIG. 3 shows the instrument as shown in FIG. 2 but without securing member in a front view, partly in section.

FIG. 4 shows part of the instrument on a bigger scale in a front view, partly in section.

FIG. 5 is a section along line V—V in FIG. 4.

FIG. 6 is a plan view on a bigger scale of the securing member without screw.

FIG. 7 shows in a plan view a slightly modified instrument according to the invention.

FIG. 8 is a section along line VIII—VIII of FIG. 7.

FIG. 9 shows the instrument according to FIG. 7 in an end view.

The instrument as shown in FIGS. 2-6 inclusive comprises two support members 1a, 1b which are mutually connected by means of a screw spindle 2, which as appears from FIG. 2 has a threaded portion 3, which engages an internal thread 4 of one of the support members 1b. The screw spindle 2 passes through said internally threaded hole, and outside the latter it has a key handle 5. The unthreaded portion 6 of the screw spindle passes through an unthreaded bore 7 in the other support member 1a and also in this case the projecting end of the spindle is formed to a key handle 5. The unthreaded portion of the screw spindle is provdied with two circumferential grooves 8a, 8b.

In order to make it possible to rotate the spindle but prevent the displacement thereof in relation to the support member 1a the latter comprises a means to be described which is intended to engage the groove.

By this arrangement the support members 1a, 1b will move away from each oter when the screw spindle is rotated in one direction and towards each other when the screw spindle is rotated in the opposite direction.

As will appear more clearly from FIG. 1 and FIG. 4 each support member 1a, 1b is pivotally connected to a securing member 9 which as appears from FIG. 2(2) and FIG. 3 consists of a block of a substantially parallelepipedic shape. For this pivotal connection the support member in question has a stud 10 and said studs extend through corresponding holes of the securing member 9 in question (see FIG. 2(b)). Each stud has a transverse slot-shaped hole 11 of greater width at each end than in the middle which—when the support member and the securing member are joined—communicates with a through, narrower hole 12 extending from the upper surface of the securing member and which as appears from FIG. 3 has an upper portion 13 which is wider and threaded.

A locking member 14, which has an outer threaded portion 15 for engaging the thread 13 of the securing member and a tapered portion 16 as well as a preferably cylindrical narrower portion 17 is threaded according to FIGS. 2(b) and 3, and it is thus obvious that the locking member by abutment against one of the axial limits of the hole 11 (see FIG. 2(b)) limits the displacement of the securing member 9 in relation to the stud 10.

When the locking member 14 only is screwed in to such an extent that the narrower part of the tapered portion thereof contacts the wall of the stud which surrounds the hole the securing member and the support member will be free to move relative to each other in the length direction of the stud but this movement will successively diminish when the locking member is screwed in.

The more the locking member is screwed in the more the support member and the securing member will approach each other and as will appear from the following the parts are measured in such a manner that a locking action is accomplished just before the locking member is fully screwed in. As appears from FIG. 3 the hole 11 has such a shape in the transverse direction thereof that the support member and the securing member may fulfill a restricted pivotal movement relative to each other as long as the locking member is not fully tightened. In the securing member 9 there is further provided a through hole 18 extending from the upper side thereof and which as seen in FIG. 6 has the centre thereof located at a distance from the surface 19 of the securing member adjacent to the support member which is less than the radius of the hole whereby the hole in question will be open in direction towards the support member. A so called bone screw 20 the lower end (not shown) of which is threaded and the upper end of which has a plurality of circumferential centimeter indications 21 (see FIG. 1) projects through the mole 18.

The bone screws are intended to be screwed into the actual vertebrae and from the foregoing it is apparent that the securing members 9 can be displaced relative to the bone screws when the surface 19 of the securing members is located at a distance from the corresponding surface 22 of the support member (see FIG. 4) which exceeds the difference between the radius of the bone screw and the distance from the surface 19 to the centre of the hole 18, i.e. the locking member 14 may only be partly screwed in. In this position of the locking member the securing members thus may be freely displaced in relation to the bone screws and the securing member may be pivoted in relation to the support member.

When however the locking member 14 is screwed in such that the tapered surface 16 thereof will successively act against one of the end surfaces which limit the hole of the stud a locking action takes place which prevents said pivoting movement as well as movement of the bone screw. The first-mentioned effect is increased by a plurality of co-operating ridges and grooves 23,24 in the surfaces of the securing member and the support member which face each other, and the latter effect may be secured by means of the arrangement shown in FIG. 4. According to this arrangement the bone screw in the portion thereof which is adjacent to and extends into the the securing member has a plurality of circumferential grooves 25 located at certain axial distances from each other, and to the upper side of the securing member and preferably countersunk into the latter there is pivotally mounted and axially secured a bolt 26 having a circular head 27 the thickness of which being substantially equal to the width of the grooves and having in the periphery thereof a recess 28 which in a first angular position of the bolt by communication with the hole 18 for the bone screw allows the latter to be freely displaced but in a second angular position when the non-recessed portion of the bolt head is in registry with the hole for the bone-screw prevents such a displacement. The bolt has just like the locking member 14 an internal key socket 29. It is obvious that by these arrangements it is possible to fix the angular position of the support member relative to the securing member as well as to fix the bone screw in the actual position from one direction and by using simple tools for instance so called insex wrenches.

In order to be able to fix in the same simple manner also the position of the support members relative to each other each suport member 1a, 1b has a clamping device provided to act aganst the screw spindle. The support member 1b which has the internal thread 4 has for this purpose a slotted portion 30 to form two resilient portions 31 and 32 which are located one above the other one and which in a manner known per se can be forced towards each by means of a clamp bolt 33. The other support member 1a has a similar slotted portion but the distance between the centre of the bore 7 for the screw spindle and the centre of the clamp bolt 34 is so measured that a preferably not threaded portion of the clamp bolt 34 will protrude into the groove 8b or 8a which means that said clamp bolt will fulfill a double function, i.e. as a locking means to prevent rotation of the screw spindle relative to the support member 1a and as a means to prevent the axial displacement of the screw spindle relative to the support member in question. Owing to the fact that the screw spindle has two grooves 8a, 8b it may be selectively used for left or right hand connection.

In order to further lock an adjustment of the screw spindle the latter may according to FIG. 2(a) be provided with a number of longitudinal grooves 35 located at a certain angular distance, for instance 90°, from each other and the head 36 of the clamp bolt 33 in question then is free to engage one of said grooves as seen in FIG. 5 to obtain said locking action.

Finally it may be appropriate to lock the actual securing member against rotation relative to the bone screw 20 in question and for that purpose each securing member 9 has a through hole 37, extending from the upper side thereof and through this hole a pin, a screw or the like can be driven into the actual vertebrae.

As appears from FIG. 1 the instrument usually consists of two separate units each comprising two support members mutually connected by means of a screw spindle and securing members and bone screws connected thereto and fixing can thus be accomplished between two vertebrae with intermediate vertebrae or vertebrae and all operations may be effected from one position and without operating too deep in the body of the patient.

The instrument now described is operated in the following manner:

The bone screws 20 are first screwed into the vertebrae which are to be connected. The support member and the securing member connected thereto is then by means of the screw spindle 2 moved to such a position that the instrument can be slid onto the already located bone screws. The locking members 14 are then loosened to such extent that the bone screws may be introduced through the openings 18 and the bolt 26 is in such an angular position that the recess 28 thereof coincides with the hole 18 and in this position the support members may be swung in relation to the securing members. The bolts 26 having the heads 27 are then turned such that said heads engage one of the grooves 25. A first axial locking then occurs between the actual bone screw and the securing means in question. This locking however does not prevent a further tightening of the bone screws which is a very important feature of the new instrument. After such a tightening the vertebrae may be moved by operating the bone screws.

When the intended adjustment of the vertebrae has taken place the position is fixed by tightening the locking members 14. The securing member is then pressed against the support member and a locking of the bone screws then occurs and simultaneously the securing member is fixed against pivoting in relation to the support member. To prevent a turning movement of the securing member relative to the bone screw the former preferably has a hole 37 through which an anchoring means such as a pin or a screw provided to engage the vertebrae can be introduced. When the screw spindle 2 has been fixed against turning by tightening the clamp bolts 33 and 34 and this locking preferably has been locked in that the heads 36 of the clamp bolts 33 have been brought to engage any of the grooves 35 the intended locking has been carried out. In a manner known per se the dispensable upper portion of the bone screws may be removed by cutting by means of a suitable tool. As appears from FIG. 1 two instrument units are generally used and it is of course possible to adjust and fix said units relative to each other by means of connection means not shown.

In the modified instrument shown in FIGS. 7-9 inclusive the support members 1a, 1b are secured relative to each other by means of a locking screw 40 acting against the screw spindle (see FIG. 8) and in order to lock the support members to the securing members and at the same time also lock the bone screws in holes 18 the arrangement illustrated in FIGS. 7 and 8 is used. In contradistinction to the embodiment just described the stud which allows the pivoting of the support member relative to the securing member has no transverse opening but the pivot stud 41 instead has an annular groove 42 with a conical surface 43 against which the conical portions 16 of two locking members 14 of the kind described act. It is evident that a tightening of said locking members brings forth the same double-effect as just described, i.e. that the support members 1a, 1b and the securing members 9a, 9b are locked in their actual angular position relative to each other and that the securing members during said tightening are displaced a little bit towards the support members which brings forth a locking of the bone screws 20 in their set positions. Also in this case the bone screws preferably have a number of axially spaced grooves for cooperation with a bolt (such as bolt 26 of FIG. 4) with a head 27 to accomplish a first securing against displacement and it is also clear that it also in this case is possible to tighten the bone-screws as long as the locking members 14 are not fully tightened. In order to increase the action of the locking members 14 the groove 42 in the pivot stud 41 in question preferably has such a depth (see FIG. 8) that the conical portions 16 of the locking members 14 will act against the conical surface 43 of the groove as well as against the bottom 44 thereof.

I claim:

1. A fixing instrument for securing two vertabrae in fixed relative positions during spinal surgery, comprising:
   a. a screw spindle having a threaded portion;
   b. first and second support members rotatably mounted on said screw spindle, said second support member having a threaded bore threadably engaged with said threaded portion of said screw spindle so that rotation of said screw spindle relative to said first and second members causes said first and second support members to move relative to one another along the length of said screw spindle, each of said support members including a stud fixed thereto, said stud having an axis substantially perpendicular to the length of said screw spindle, each of said studs including a transverse slot having axially opposed side walls and extending radially through said stud;
   c. first and second bone screws; and
   d. first and second securing means for respectively securing said first and second bone screws to said first and second support members, each of said securing means including:
   a securing member pivotally mounted on said stud of said respective support member and having a locking hole aligned with said transverse slot of said respective stud, said securing member also including a surface portion facing said respective support member and a substantially cylindrical bone screw hole adjacent said surface portion for holding said respective bone screw, said bone screw hole having a central axis spaced from said surface portion by a distance less than the radius of said bone screw hole so that a peripheral portion of said bone screw held in said bone screw hole protrudes from said surface portion of said securing member, for permitting said peripheral portion of said respective bone screw to engage with said surface portion of said respective support member and thereby prevent movement of said bone screw relative to said respective support member, and
   locking means movably disposed in said locking hole and said respective aligned slot for selectively restraining movement of said securing member relative to said respective support member, said locking means including a locking member having a tapered surface portion providing variable clearance between sid locking member and said side walls of said slot, said tapered surface portion having a maximum cross section engageable with both of said side walls to clamp said securing member to said respective stud and thereby engage said peripheral portion of said respective bone screw with the surface portion of the respective support member.

2. The fixing instrument of claim 1, wherein each of said locking holes includes a threaded portion and each of said locking members is threadably engaged with said threaded portion of said respective locking hole.

3. The fixing instrument of claim 1, wherein each of said support members includes:
   a clamp portion having two resilient members separated by a slot; and
   a clamp bolt passing through said resilient members to force said resilient members toward one another and thereby clamp said respective support member to said screw spindle.

4. The fixing instrument of claim 3, wherein:
said threaded portion of said screw spindle includes at least one groove extending along the length of said screw spindle; and
said clamp bolt of said second support member includes a head portion engageable with said groove to prevent said screw spindle from rotating relative to said second support member.

5. The fixing instrument of claim 3, wherein:
said screw spindle includes a circumferential groove proximate said first support member; and
at least a portion of said clamp bolt of said first support member protrudes into said circumferential groove to prevent said screw spindle from moving relative to said first support member along the length of said screw spindle.

6. A fixing instrument for securing two vertabrae in fixed relative positions during spinal surgery, comprising:
   a. a screw spindle having a threaded portion;

b. first and second support members rotatably mounted on said screw spindle, said second support member having a threaded bore threadably engaged with said threaded portion of said screw spindle so that rotation of said screw spindle relative to said first and second members causes said first and second support members to move relative to one another along the length of said screw spindle, each of said support members including a stud fixed thereto, said stud having an axis substantially perpendicular to the length of said screw spindle, each of said studs including a tapered circumferential groove;

c. first and second bone screws; and d. first and second securing means for respectively securing said first and second bone screws to said first and second support members, each of said securing means including:

a securing member pivotally mounted on said stud of said respective support member, said securing member also including a surface portion facing said respective support member and a substantially cylindrical bone screw hole adjacent said surface portion for holding said respective bone screw, said bone screw hole having a central axis spaced from said surface portion by a distance less than the radius of said bone screw hole so that a peripheral portion of said bone screw held in said bone screw hole protrudes from said surface portion of said securing member, for permitting said peripheral portion of said respective bone screw to engage with said surface portion of said respective support member and thereby prevent movement of said bone screw relative to said respective support member, and locking means for selectively restraining movement of said securing member relative to said respective support member, said locking means including at least one locking member threadably disposed in said securing member and having a tapered surface portion providing variable clearance between said locking member and said groove of said respective stud, said tapered surface portion having a maximum cross section engageable with said groove to clamp said securing member to said respective stud and thereby engage said peripheral portion of said respective bone screw with the surface portion of the respective support member.

7. The fixing instrument of claim 6, wherein said locking means includes a pair of said locking members threadably disposed in each of said securing members on diametrically opposite sides of said respective stud.

8. The fixing instrument of claim 6, wherein each of said support members includes locking screw for locking said respective support member to said screw spindle.

9. The fixing instrument of any of claims 1, 2, 6, or 7, wherein said surface portion of each of said securing members and a portion of each of said support members facing said surface portion of said respective securing members have cooperating ridges and depressions for engagement between said respective support member and securing member.

10. The fixing instrument of claim 9, wherein said ridges and depressions extend radially with respect to said axis of said stud of said respective support member.

11. The fixing instrument of claim 9, wherein said ridges and depressions are positioned on a side of said stud opposite said bone screw hole of said respective securing member.

12. The fixing instrument of any of claims 1, 2, 6, or 7, wherein:

each of said bone screws includes a plurality of axially spaced circumferential locking grooves; and each of said securing members includes a bone screw-locking member rotatable about a pivot axis substantially parallel to said central axis of said bone screw hole, each of said bone screw-locking members having a head portion of substantially the same thickness as the axial width of said locking grooves, said head portion including a substantially circular edge with a recess therein, said head portion being rotatable between a first angular position in which said recess is aligned with said bone screw hole to permit axial movement of said bone screw relative to said securing member and a second angular position in which said edge engages one of said locking grooves of said bone screw to restrain axial movement of said bone screw.

* * * * *